United States Patent [19]

Hattler et al.

[11] 4,406,656
[45] Sep. 27, 1983

[54] VENOUS CATHETER HAVING COLLAPSIBLE MULTI-LUMENS

[75] Inventors: Brack G. Hattler, Denver; Ronnie D. Richards, Arvada; William J. Horgan, Littleton, all of Colo.

[73] Assignee: Brack Gillium Hattler, Denver, Colo.

[21] Appl. No.: 268,766

[22] Filed: Jun. 1, 1981

[51] Int. Cl.³ ............................................. A61M 25/00
[52] U.S. Cl. ...................................... 604/280; 604/43; 604/282; 604/96; 604/158
[58] Field of Search ...................... 128/214.4, 240, 241, 128/348–350 R; 604/43–45, 96, 280–284, 158–163

[56] References Cited

U.S. PATENT DOCUMENTS

| | | | |
|---|---|---|---|
| 1,089,805 | 3/1914 | Wolf | 128/349 R |
| 1,596,754 | 8/1926 | Moschelle | 128/350 R |
| 1,696,018 | 12/1928 | Schellberg | 128/240 |
| 3,433,215 | 3/1969 | Silverman | 128/214.4 |
| 3,605,749 | 9/1971 | Heimlich | 128/349 R |
| 3,703,174 | 11/1972 | Smith | 128/214.4 |
| 4,072,146 | 2/1978 | Howes | 128/214.4 X |
| 4,154,227 | 5/1979 | Krause et al. | 128/349 B |
| 4,292,974 | 10/1981 | Fogarty et al. | 128/344 |

Primary Examiner—Dalton L. Truluck
Attorney, Agent, or Firm—Robert C. Dorr

[57] ABSTRACT

A venous catheter having a central flexible lumen with a formed fluid passageway therein and a plurality of collapsible lumens mounted around the periphery of the central flexible lumen also having formed fluid passageways therein. The central flexible lumen being formed of material which is capable of retaining its shape with or without fluid flowing therethrough. Each collapsible lumen being formed from material which is normally collapsed in a small cross-sectional area and which is further capable of expanding when fluid is flowing therein to a cross-sectional area much greater than that when collapsed. The catheter being capable of being inserted through the center of an insertion needle in the collapsed state into the vein of a patient.

8 Claims, 15 Drawing Figures

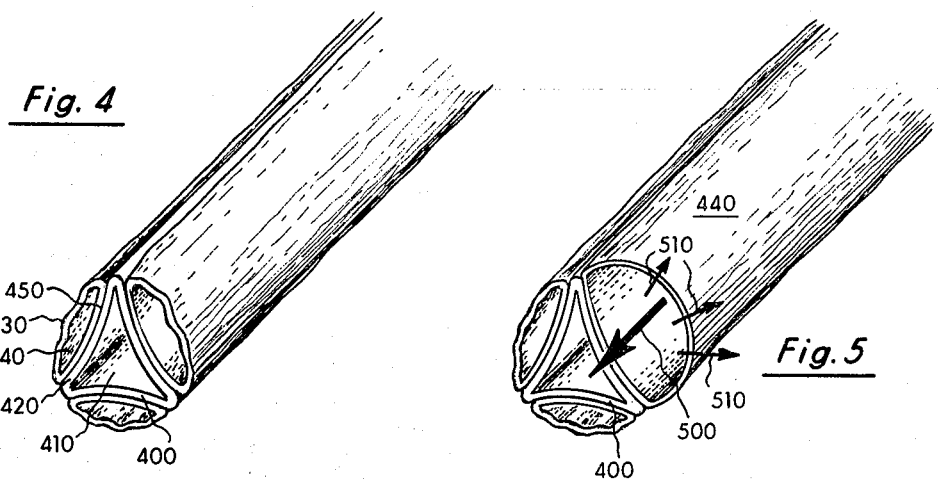
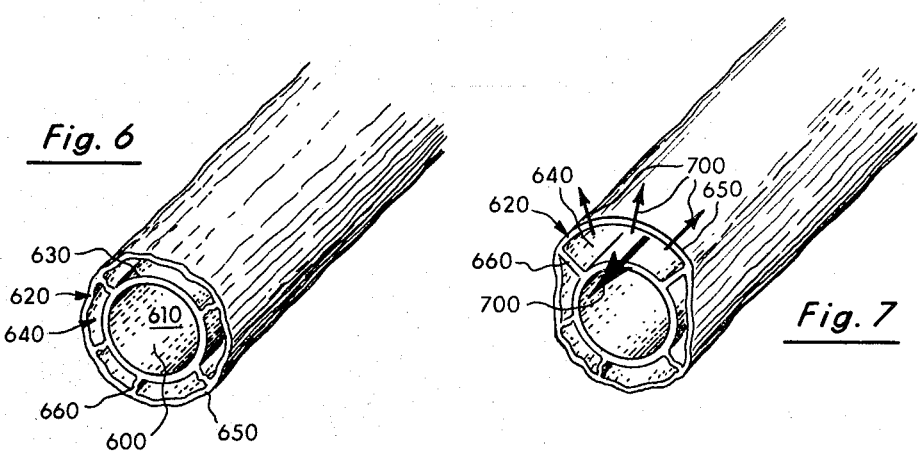
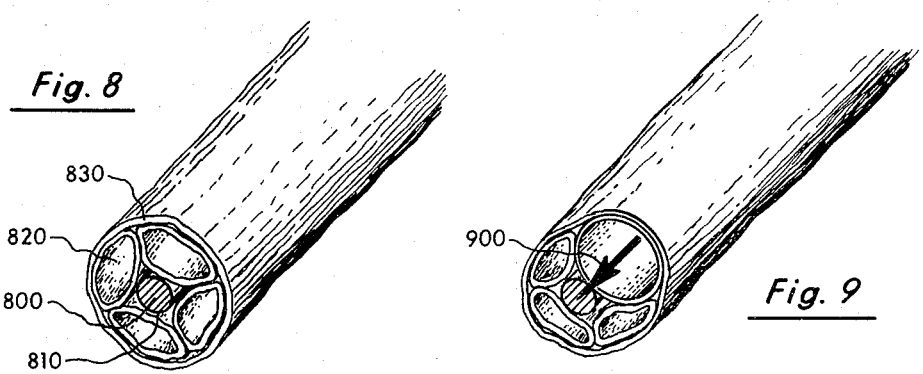

VENOUS CATHETER HAVING COLLAPSIBLE MULTI-LUMENS

FIELD OF THE INVENTION

This invention relates to catheters and, in particular, to venous catheters having multi-lumens.

BACKGROUND OF THE ART

Catheters of many types and configurations have been known and have been utilized for a number of years. Venous catheters function to carry fluids into and out from the vein of a patient. One problem associated with venous catheters is the physical discomfort to the patient caused by the insertion of the catheter into the vein and the maintenance of the catheter in the patient for a period of time. Another problem associated with venous catheters is one of infection to the patient. These problems become magnified when a number of venous catheters are inserted either at the same time or over a period of time. An overall solution, therefore, is to arrive at a venous catheter having multi-lumens (i.e., fluid carrying passageways) in a single catheter. Utilization of a catheter with multi-lumens would minimize the problems associated with patient discomfort and the risk of infection.

A prior art search, conducted by the inventor of the present invention, disclosed various types of multi-lumen catheters having various functions. The results of this search are set forth as follows:

| Inventor | U.S. Pat. No. | Issue Date |
|---|---|---|
| H. H. Khalil | 3,359,974 | Dec. 26, 1967 |
| Ballard | 3,055,361 | Sept. 25, 1962 |
| L. J. Bielinski | 3,437,088 | April 8, 1969 |
| Shepherd et al | 3,566,874 | March 2, 1971 |
| Jose M. R. Delgado | 3,640,269 | February 8, 1972 |
| T. H. Shepherd | 3,695,921 | October 3, 1972 |
| Norton et al | 3,726,281 | April 10, 1973 |
| Schlesinger | 3,805,794 | April 23, 1974 |
| Spinosa et al | 3,815,608 | June 11, 1974 |
| Long | 3,867,945 | February 25, 1975 |
| Ross | 3,885,567 | May 27, 1975 |
| Blake et al | 3,995,623 | Dec. 7, 1976 |
| Thow | 4,057,065 | Nov. 8, 1977 |
| Howes | 4,072,146 | Feb. 7, 1978 |
| Sorenson et al | 4,099,528 | July 11, 1978 |
| Frisch | 4,100,246 | July 11, 1978 |
| McWhorter | 4,106,509 | August 15, 1978 |
| Kenigsberg | 4,168,703 | Sept. 25, 1979 |
| Betancourt | 4,180,076 | Dec. 25, 1979 |
| Grimsrud | 4,203,436 | May 20, 1980 |
| Sagae et al | 4,217,895 | August 19, 1980 |

The 1978 patent issued to Howes (U.S. Pat. No. 4,072,146) relates to a venous catheter device having a plurality of independent fluid conveying lumens housed within a single catheter. The multi-lumen catheter of Howes is designed to have an outer diameter slightly smaller than the inner diameter of the insertion needle so that the catheter can be inserted through the needle. Each of the independent lumens are encased within an outer tube.

In operation, the Howes catheter permits two or more fluids to be infused simultaneously into the blood stream at discrete spacings of at least one centimeter. This prevents any mixing problem.

The 1978 patent issued to Sorenson et al (U.S. Pat. No. 4,099,528) relates to a double lumen cannula for separately injecting fluids into the blood vessel or withdrawing fluids from a blood vessel. The double lumen represents concentric passageways.

The 1976 patent issued to Blake et al (U.S. Pat. No. 3,995,623) relates to a multi-lumen catheter containing a number of lead wires and a permanent stylet wire of graduated stiffness.

The patents issued to Shepherd et al (U.S. Pat. No. 3,566,874), Shepherd et al (U.S. Pat. No. 3,695,921), Norton (U.S. Pat. No. 3,726,281), Long (U.S. Pat. No. 3,867,945) and Spinosa (U.S. Pat. No. 3,815,608) all relate to multi-lumen catheters of differing configurations for use as ureteral catheters. In all of these embodiments, a central lumen is provided with one or more lumens disposed there around and formed integral with the primary catheter bodies.

The patents issued to Bielinski (U.S. Pat. No. 3,437,088), Schlesinger (U.S. Pat. No. 3,805,794), Thow (U.S. Pat. No. 4,057,065), Frisch (U.S. Pat. No. 4,100,246), McWhorter (U.S. Pat. No. 4,106,509), Kenigsberg (U.S. Pat. No. 4,168,703), Betancourt (U.S. Pat. No. 4,180,076) and Ross (U.S. Pat. No. 3,885,567) all relate to catheters for entry into internal body organs such as the stomach and all disclose a multi-lumen apparatus or device. Bielinski discloses a lumen arrangement of four tubes, Schlesinger discloses a central lumen with a smaller lumen, Thow discloses four lumens of differeing diameters vertically arranged within a spotty portion, Frisch also discloses four vertically arranged lumens of differing diameters, McWhorter relates to a balloon catheter having two lumens, Kenigsberg discloses a gastroesophaged reflux diagnostic tool having three lumens, Betancourt provides a nasogastric catheter having three lumens, and finally Ross teaches the use of a gastrointestinal aspirator pump having as many as four lumens in one embodiment.

The patents issued to Shepherd et al (U.S. Pat. No. 3,695,921), Khalil (U.S. Pat. No. 3,359,974), Delgardo (U.S. Pat. No. 3,640,269), Grimsrud (U.S. Pat. No. 4,203,436), and Sagae et al all relate to multi-passageway catheters or other similar devices.

The search was made in Class 128, subclasses 214, 214.2, 214.4, 347, 348, 349R and 349B.

None of the prior art patents uncovered in the search, sets forth a catheter suitable for insertion through the center of the needle into the vein of a patient wherein each lumen is capable of normal fluid flow (i.e., comparable to the flow of fluids through a single lumen catheter). The Howes catheter set forth above does have a number of lumens and can be inserted through the inside of an insertion needle. Howes, however, uses lumens with small fluid passageways which do not compare to the fluid flows in conventional single lumen catheters. A conventional single lumen venous catheter has an internal fluid passageway with a diameter comparable to the inner diameter of the insertion needle. Hence, a single lumen venous catheter has what is termed a "normal" fluid carrying capacity. The Howes' multi-lumen catheter has a number of lumens having passageways with reduced diameters and, therefore, the fluid flow rate is significantly reduced over the normal flow rate of a single lumen catheter. It is to be understood that insertion needles and conventional single lumen venous catheters come in different sized passageways.

It is desired to achieve a multi-lumen catheter which is capable of insertion through conventional insertion needles and yet, after insertion each lumen is capable of fluid carrying capacity comparable to that of a single lumen catheter.

It is therefore an object of the present invention to provide a collapsible multi-lumen catheter which, like a conventional single lumen catheter, is capable of insertion through the center of an insertion needle into the vein of a patient. Yet, after insertion, each lumen is capable of carrying fluid in flow rates comparable to that of conventional single lumen catheters. This is accomplished in the present invention by having a plurality of collapsible lumens disposed around a central flexible lumen wherein each collapsible lumen expands outwardly under the pressure of fluid flow and when fluid flow is absent, the lumen collapses to a smaller cross-sectional area. None of the prior art patents set forth a catheter utilizing collapsible lumens which expand under the pressure of fluid flow after insertion into the patient.

SUMMARY OF THE INVENTION

This invention provides an improved multi-lumen catheter adapted to be inserted into the vein of a patient through a conventionally sized insertion needle, yet, upon insertion, each lumen being capable of substantially functioning as a conventionally sized single lumen catheter.

In accordance with a preferred embodiment of this invention, an elongated central flexible lumen is provided having a formed fluid passageway therein, the material comprising the central flexible lumen having sufficient resiliency to maintain its shape whether or not fluid is flowing therethrough. A plurality of elongated collapsible lumens are affixed to the outer periphery of the central flexible lumen. Each collapsible lumen being formed from material having sufficient resiliency to expand to an increased cross-sectional area under pressure of fluid flowing therethrough and to return to a substantially fully collapsed state after passage of the fluid. In the fully collapsed state, the central lumen with the plurality of elongated collapsible lumens disposed therearound is capable of being inserted through the center of a conventionally sized insertion needle.

These and other features, objects and advantages of the present invention will be more readily understood in view of the following detailed description which will make reference to the attached drawing which is set forth next.

DESCRIPTION OF THE DRAWING

FIG. 4 sets forth, in cross-sectional perpsective view, a second embodiment of the catheter of the present invention similar to the type shown in FIG. 2 but having each collapsible lumen independently constructed;

FIG. 5 sets forth, in cross-sectional perspective view, the catheter shown in FIG. 4 with one of the collapsible lumens fully expanded under the pressure of fluid flow;

FIG. 6 sets forth, in cross-sectional perspective view, a third embodiment of the catheter of the present invention wherein the central flexible lumen is circular in cross-section and contains a number of collapsible lumens concentrically disposed therearound;

FIG. 7 sets forth, in cross-sectional perspective view, the catheter of FIG. 6 in which one of the collapsible lumens is fully expanded under the pressure of fluid flow;

FIG. 8 sets forth, in cross-sectional perspective view, a fourth embodiment of the catheter of the present invention wherein a flexible central rod provides support to a plurality of collapsible lumens disposed therearound;

FIG. 9 sets forth, in cross-sectional perspective view, the catheter of FIG. 8 in which one of the lumens is fully expanded under the pressure of fluid flow;

GENERAL DESCRIPTION

Figure 1:
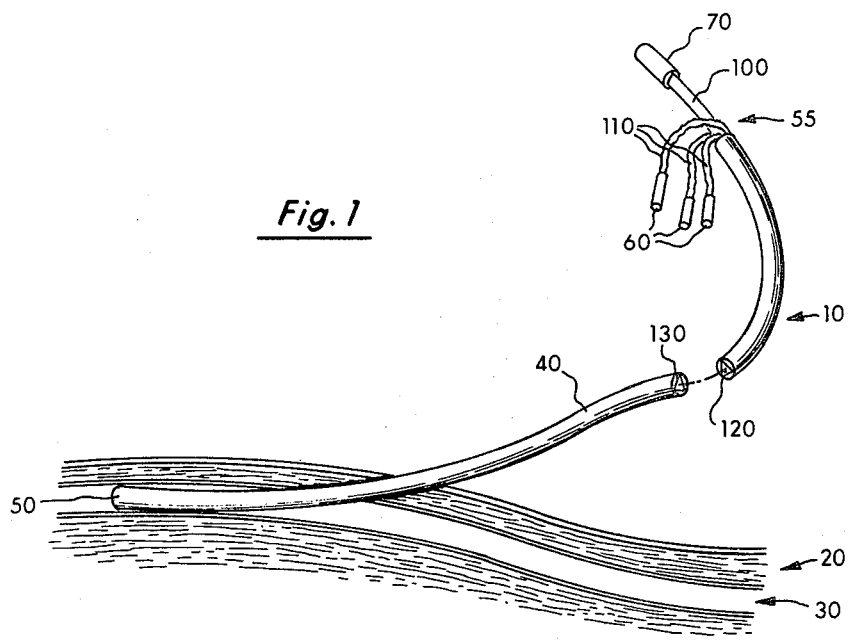
In FIG. 1 is shown the catheter of the present invention fully inserted into the vein of a patient.

In FIG. 1, the catheter 10 of the present invention is shown fully inserted through the skin 20 of a person and into the person's vein 30. The catheter 10 of the present invention includes an elongated body portion having a distal end 50 in the vein 30. A plurality of adapters 60 and adapters 70 are provided on the opposing end 55 of the catheter 10 for conventionally interconnecting with conventional fluid sources or other devices. For example, such conventional sources or devices may include an intravenous bottle connected to the adapter 60 by means of suitable plumbing, central venous pressure (CVP) monitoring device, sources for fluid or drug injection, and sources for blood sampling.

Under the teachings of the present invention, the catheter 10 of the present invention can include a central lumen 100 having disposed therearound a plurality of collapsible lumens 110. The central lumen 100 is formed of conventional, flexible and heat pliable material wherein the passageway 120 retains its shape whether or not fluids flow therethrough. Attached to the outer end of lumen 100 is adapter 70.

Disposed around the central lumen 100, which as shown in FIG. 1 has a triangular-shaped cross-section, is a collapsible lumen 110 disposed on each side of the triangular-shaped central lumen 100. Each collapsible lumen 110 is made from sufficiently elastic and resilient material so that when fluid is not flowing through the collapsible passageway 130, the lumen 110 collapses about itself by reducing the size of the lumen, in cross-section, to a smaller size. When fluid is flowing through the passageway 130 of the collapsible lumen 110, the outerwalls of the lumen 110 expand outwardly from the forces of the fluid to a greater diameter in order to allow passage of the fluid therethrough. Under the teachings of the present invention, and as will be explained more fully, the collapsible lumens are designed to expand to a greater diameter when fluid flow occurs in the passageway 130 of each collapsible lumen 110. Because of the collapsed nature of the outer lumens 110, the cross-sectional area of the catheter 10 of the present invention approximates the cross-sectional area of conventional single lumen catheters.

As with all multi-lumen catheters, the passageways of the multi-lumen catheter 10 of the present invention are totally independent of each other so that fluids flowing in each passageway will not mix together. The multi-lumen catheter 10 of the present invention is further designed to permit individual use of each lumen contained therein or simultaneous use of all lumens depending on the conditions being required.

It is to be expressly understood that the configuration shown in FIG. 1 is a preferred embodiment and that modifications and variations can be made thereto as will be pointed out, but not limited to, the following.

DETAILED DESCRIPTION

Figures 2, 3:
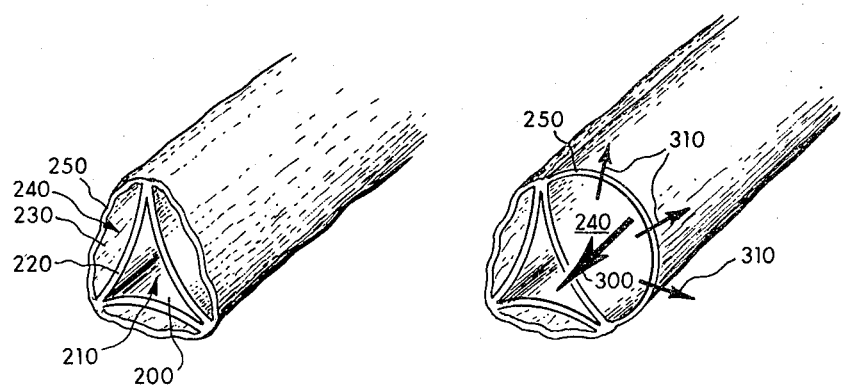
In FIG. 2 is shown, in cross-sectional perspective view, a catheter of a first embodiment having a central flexible lumen with a triangular shaped cross-section with a collapsible lumen mounted on each side.
In FIG. 3 is shown, in cross-sectional perspective view, the catheter embodiment shown in FIG. 2 wherein one of the collapsible lumens is fully expanded under the pressure of fluid flow.

In FIGS. 2 through 9 are shown various embodiments of the catheter 10 of the present invention. In FIGS. 2 and 3, the central flexible lumen 200 defines a substantially triangular-shaped, in cross-section, formed fluid passageway 210. Disposed on each side 220 of the central flexible lumen 200 is mounted at least one collapsible lumen 230 having a formed fluid passageway 240. In this embodiment, the outer edge of side 220 forms the inner edge of fluid passageway 240. The side 220 being nonexpandable. However, the side 250 of the collapsible lumen 230 is made from material having sufficient resiliency to expand outwardly as shown in FIG. 3. As illustrated by arrow 300, when fluid flows through passageway 240, the outer wall 250 expands radially outward in the direction of arrows 310 to a cross-sectional area having a much greater cross-sectional area than in the collapsed state as shown in FIG. 2. After the fluid material 300 flows through the expanded lumen 250, the lumen collapses and returns to the shape shown in FIG. 2. As can be witnessed in FIGS. 2 and 3, the sides 220 of the triangular-shaped central flexible lumen 200 is slightly concaved inwardly.

It is to be expressly understood, that although a central lumen 200 is illustrated being triangular in cross-section any member of the general class of polygons can be utilized as a central lumen 200 under the basic teachings set forth in FIGS. 2 and 3. In that event, each side of the polygon-shaped central lumen would form one side of the collapsible lumen 250.

In FIGS. 4 and 5 are shown a modified version of the catheter 10 of the present invention. The catheter shown in FIGS. 4 and 5 utilizes the same triangular shaped, in cross-section, central lumen 400 having a formed fluid passageway 410. Disposed on each side 420 of the central flexible lumen 400 is a collapsible lumen 430 having a formed fluid passageway 440 contained therein. The difference in structure between the embodiment shown in FIG. 4 and that of FIG. 2 is that each collapsible lumen 430 is self contained having one side 450 affixed to side 420 of the central lumen 400. As before, when a fluid, as represented by arrow 500, passes through the fluid passageway of collapsible lumen 440, it expands radially outwardly in the direction of arrows 510 to a much increased cross-sectional area than in the collapsed state.

In FIGS. 6 and 7 is shown yet another preferred embodiment wherein the central lumen 600 has the formed passageway 610 which is circular in cross-section. The central lumen 600 has a plurality of collapsible lumens 620 disposed around the outer circumference 630 of the central lumen 600. The collapsible lumens 620 may have formed fluid passageways 640 of equal cross-sectional area or of different cross-sectional areas (as shown in FIG. 6). The central lumen 600 is disposed centrally in an outer sheath 650 and is separated therefrom by a plurality of vertical side walls 660 which form the collapsible lumens 620. As shown in FIG. 7, when a fluid as represented by arrow 700, flows through one of the collapsible lumens 620, the lumen rapidly expands outwardly in the direction of arrows 700 to form a fluid passageway 650 of much increased cross-sectional area. In achieving this increased cross-sectional area, the vertical side walls 660 expand outwardly as well as the outer sheath 650 in the vicinity of the lumen carrying the fluid 700.

Yet another embodiment of the multi-lumen catheter 10 of the present invention is shown in FIGS. 8 and 9 wherein a central guide 800 is formed of a somewhat stiff material such as the material utilized in the construction of the central flexible lumens in FIGS. 2 through 7, but being of solid configuration such as that of a flexible rod. Disposed around the outer-surface 810 of the guide 800 are a plurality of collapsible lumens 820 of the present invention which are in turn covered by an outer sheath 830. Sheath 830 is formed of the same material as each of the collapsible lumens 820 so that, as shown in FIG. 9, when a fluid 900 flows through a collapsed lumen 820, it radially expands outwardly, in all directions, so that not only the collapsible lumen 820 expands outwardly, but also the covering sheath 830 expands outwardly in the direction thereof.

It is to be noted, at this time, that the central flexible lumen 200, in FIGS. 2 and 3, 400 in FIGS. 4 and 5, and 600 in FIGS. 6 and 7 all perform a similar function as does the guide in FIGS. 8 and 9. All provide sufficient structural support for the catheter 10 of the present invention so that the catheter 10 can be handled as are conventional catheters. Without the provision of the central lumens or a guide 800, the collapsible lumens of the present invention would run the risk of being kinked or bent at one or more locations and thereby prevent the proper flow of fluids either into or out from the vein 30. A certain degree of stiffness or rigidity is needed yet, at the same time, providing sufficient flexibility to be medically useful and comfortable for the patient. Hence, the materials selected for the present invention for the central flexible lumen or guide are such that the multi-lumen catheter of the present invention is capable of being handled the same as the conventional catheter. Without this, structural support, the collapsible lumens would be difficult to handle.

Figure 10:
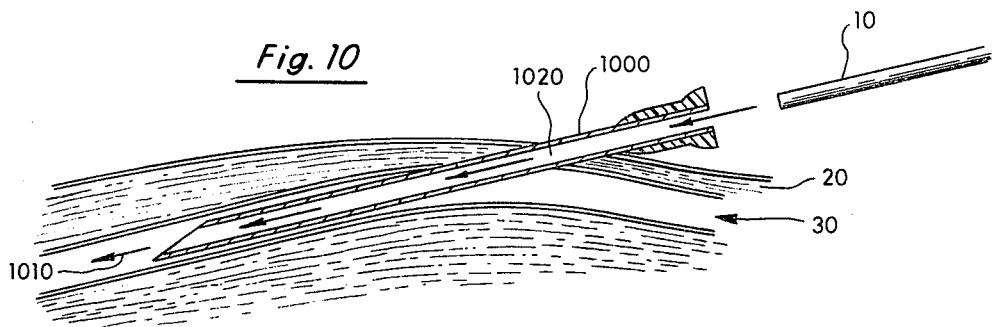
FIG. 10 illustrates, in cross-section, the insertion of the catheter of the present invention through the center of a conventional insertion needle into the vein of a patient.

In FIG. 10, the catheter 10 of the present invention is shown being inserted through a needle 1000 already inserted into vein 30 through skin 20. In actual operation, the needle 1000 is first inserted in the direction of arrows 1010 into the vein 30. In the next step, the catheter 10 of the present invention is inserted through the hollow center portion 1020 of needle 1000 in the direction of arrows 1010 until the catheter is fully inserted into the vein 30 as shown in FIG. 1. The needle 1000 is then removed from the vein 30 and the skin 20 of the patient in the direction opposite of the direction of arrows 1010. It is to be understood that some conventional needles 1000 could be removed by breaking along a longitudinal score line. Under the teachings of the present invention, and as discussed subsequently, the catheter 10 in the collapsed states as shown in FIGS. 2, 4, 6, and 8 have a combined cross-sectional area less than the inner cross-sectional area of needle 1000. After insertion, and after the removal of the needle 1000, however, and as shown in FIGS. 3, 5, 7, and 9, the catheter 10 of the present invention can selectively expand either with one collapsible lumen or with all collapsible lumens at any given time. At this time of expansion the catheter has a much greater cross-sectional area than the needle 1000. The nature of the skin 20 of the patient is such that as the collapsed multi-lumens expand outwardly due to fluid flow, the skin 20 is resilient enough to accomodate the expansion without tearing the skin.

As evident from the above disclosure, the catheter 10 of the present invention carrying multi-collapsible lumens can be conventionally inserted through a needle. Yet, once inserted the collapsible lumens can expand, under fluid pressure, to a size greater than the diameter of the insertion needle.

Figure 11:
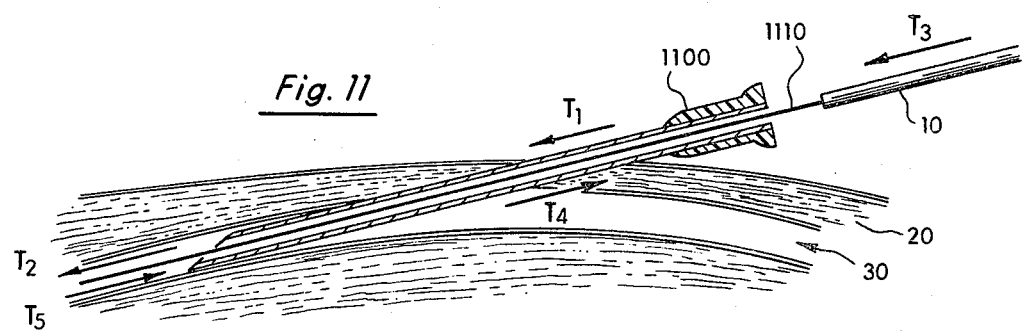
FIG. 11 illustrates, in cross-section, a second technique for insertion of the catheter of the present invention through the center of an insertion needle and into the vein of a patient by means of a guide rod.

In FIG. 11, is shown an alternate approach for insertion of the catheter 10 of the present invention. First, during time $T_1$, the needle 1100 is inserted into the skin 20 of a patient and into vein 30 thereof. During time $T_2$, a guide wire 1110 is inserted through the needle 1100 and into the vein 30. The catheter 10 having a configuration such as shown in FIGS. 2, 4, or 6, has the central flexible lumen inserted over the guidewire 1110 and through the center of needle 1100 and into the vein 30. During time $T_4$, the needle 1100 is removed from the catheter 10. Then, during time $T_5$, the guidewire 1110 is removed from the interior of the catheter. By using this alternate approach for insertion, the catheter 10 of the present invention can be accurately inserted.

It is to be expressly understood that in addition to the techniques shown in FIGS. 10 and 11, the catheter 10 of the present invention can be conventionally placed into a vein through a surgical cut-down technique thereby permitting the catheter to be directly inserted into the vein.

Figure 13:
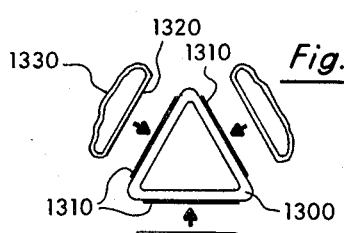
FIG. 13 illustrates, in cross-section, the construction of the catheter shown in FIG. 4.

In FIG. 13, the preferred manufacture of the multi-lumen catheter 10 of the present invention for the embodiment shown in FIGS. 4 and 5 is shown. In this preferred manufacturing technique, a central triangular-shaped lumen 1300 has placed thereon layers of adhesive 1310 to which one side 1320 of a collapsible lumen 1320 is affixed thereto. While this is a preferred manufacturing technique for one embodiment, it is to be expressly understood that other techniques such as extruding and the like could also be used.

Figure 12:
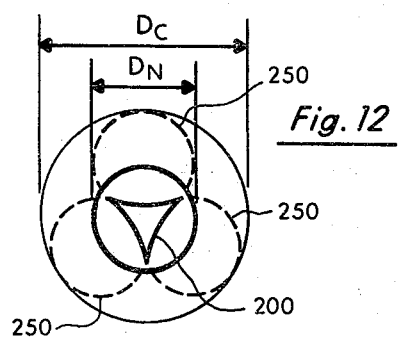
FIG. 12 illustrates, diagramatically, the catheter of the present invention having an expanded cross-sectional area significantly greater than the cross-sectional area in the collapsed state, upon insertion through the center of the needle.

In FIG. 12, the inner diameter of the needle is shown as $D_N$ and is circular in cross-section. The multi-lumen catheter of the type shown in FIGS. 2 and 3 is illustrated and in the fully collapsed state, has a cross-sectional area less in diameter than $D_N$ so that the collapsed catheter can be inserted through the inside of the insertion needle. However, after the needle is removed and if all of the collapsed lumens are fully expanded outwardly due to fluid flow, the three lumens 250 would be expanded as illustrated in FIG. 12, in a diameter $D_C$.

Under the teachings of the present invention, what is achieved is a collapsed multi-lumen catheter that can be conventionally inserted, without any discomfort than normal into the vein of a person yet, upon insertion, can be expanded outwardly. Hence, the desirability of having a single multi-lumen exhibiting substantial flowing capacity is achieved while minimizing insertion discomfort to the patient.

Figure 14:
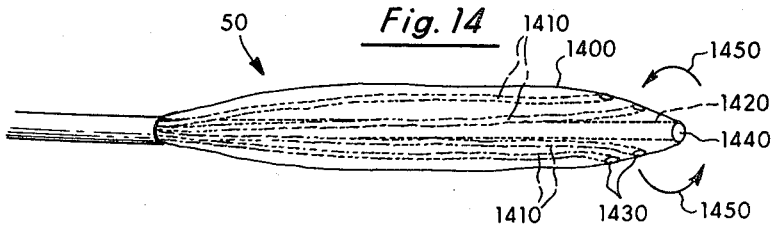
FIG. 14 illustrates a balloon sheath constructed on a distal end of the catheter of the present invention.
Figure 15:
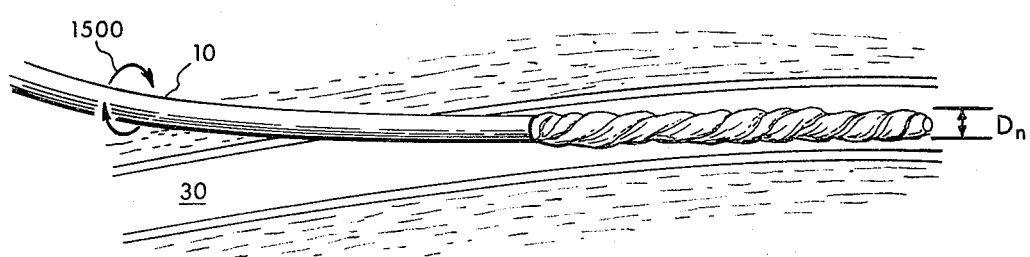
FIG. 15 sets forth the balloon sheath shown in FIG. 14 inserted into the vein of the patient.

FIGS. 14 and 15 illustrate the distal end 50 of the present invention having a balloon sheath 1400 covering a plurality of collapsible lumens 1410 disposed above the central lumen 1420. The end of each collapsible lumen 1430 terminates behind and above the end 1440 of the central lumen 1420 which is located on the longitudinal axis of the catheter. The balloon sheath is made of the same material as of each collapsible lumens 1410. Prior to insertion, the balloon sheath appears as shown in FIG. 14, but when would in direction of arrows 1450, the balloon sheath is twisted to a shape having a much smaller diameter which is less than the diameter of the needle. As shown in FIG. 15, the balloon sheath 50 can then be inserted into vein 30 (as shown in FIG. 10 or 11). Once inserted into the vein 30, the catheter 10 can be twisted in the opposite direction as shown in arrows 1500 to unwrap the balloon so that it occupies the configuration shown in FIG. 14. In summary, the balloon sheath is wrapped tightly around the central lumen 1420, is inserted into the vein 30 through a needle and upon removal of the insertion needle, the balloon sheath can be unwrapped while in the vein and be allowed to expand outwardly in the vein 30.

The above disclosure sets forth a number of embodiments illustrating preferred structural arrangements of the catheter 10 of the present invention. Other arrangements, not precisely set forth, could be practiced under the teachings of the present invention and as set forth in the following claims.

We claim:
1. A multi-lumen catheter comprising:
a plurality of collapsible lumens, each of said collapsible lumens having a formed fluid passageway therein, each of said collapsible lumens being formed from material wherein each of said collapsible lumens is capable of expanding radially outwardly under the pressure of fluid flowing therein, and wherein each of said collapsible lumens collapses when fluid is not flowing therein and wherein the total cross-sectional area of said collapsible lumens substantially increases when fluid is flowing in any of said collapsible lumens, and
means engaging each of said plurality of collapsible lumens for holding said plurality of collapsible lumens together in a bundle, said holding means being flexible, but stiff enough to prevent bending of any one of said plurality of collapsible lumens, wherein each of said collapsible lumens collapses substantially about said holding means when fluid is not flowing therein.

2. A venous catheter for insertion through a needle into a vein wherein said needle can thereupon be removed from said vein and from said catheter, said venous catheter comprising:
a plurality of collapsible lumens, each of said collapsible lumens having a formed fluid passageway therein, each of said collapsible lumens being formed from material wherein each of said collapsible lumens is capable of expanding radially outwardly under the pressure of fluid flowing therein and wherein each of said collapsible lumens collapses when fluid is not flowing therein and wherein the total cross-sectional area of said collapsible lumens substantially increases when fluid is flowing in any of said collapsible lumens, means engaging each of said plurality of collapsible lumens for holding and plurality of collapsible lumens together in a bundle, said holding means being flexible, but stiff enough to prevent bending of any one of said plurality of collapsible lumens, wherein each of said collapsible lumens collapses substantially about said holding means when fluid is not flowing therein, and the combined outer diameter of said plurality of collapsible lumens and said holding means, in the fully collapsed state, being less than the inner diameter of said needle.

3. A catheter comprising:

an elongated flexible lumen having a fluid passageway formed therein, said lumen being formed of material having sufficient resiliency to maintain its shape and wherein said passageway is capable of maintaining its configuration whether or not fluid is flowing therein, and a plurality of elongated collapsible lumens affixed to the outer periphery of said flexible lumen so that one side of each of said collapsible lumens is connected to said outer periphery, each of said elongated collapsible lumens being formed from material having a sufficient resiliency to return to a substantially fully collapsed state substantially about the outer periphery of said flexible lumen after fully expanding under pressure of fluid therethrough and wherein the total cross-sectional area of said lumens substantially increases when fluid flows through any collapsible lumen.

4. The catheter of claim 3 further comprising a thin sheath surrounding said collapsible lumens, said outer sheath being formed from material with resiliency comparable to that of the material in said plurality of collapsible lumens.

5. The catheter of claim 3 wherein said flexible lumen is substantially triangular in cross-section having a collapsible lumen affixed to each side of said flexible lumen.

6. The catheter of claim 5 wherein each outer surface of said flexible lumen forms the inner surface of the collapsible lumen attached thereto.

7. The catheter of claim 3 wherein said flexible lumen is substantially polygonal in cross-section having a collapsible lumen affixed to each side thereof.

8. The catheter of claim 3 wherein said flexible lumen is substantially circular in cross-section, said flexible lumen being substantially centered in an outer sheath having a plurality of sidewalls connecting the outer surface of said flexible lumen with the inner surface of said sheath, said plurality of collapsible lumens being formed by said sheath, said sidewalls, and said outer surface of said flexible lumen, said sheath and said sidewalls comprising said collapsible material.

* * * * *